United States Patent [19]
Fournier et al.

[11] Patent Number: 5,543,319
[45] Date of Patent: Aug. 6, 1996

[54] RECOMBINATION-PROFICIENT AVIAN/MAMMALIAN MICROCELL HYBRIDS

[75] Inventors: R. E. Keith Fournier, Mercer Island; Mark T. Groudine, Seattle; Ellen S. Dieken, Issaquah; Elliot M. Epner, Seattle, all of Wash.

[73] Assignee: Fred Hutchinson Cancer Research Center, Seattle, Wash.

[21] Appl. No.: 415,354

[22] Filed: Mar. 31, 1995

[51] Int. Cl.$^6$ .............. C12N 5/12; C12N 5/26; C12N 15/08

[52] U.S. Cl. .............. 435/240.26; 435/172.2; 435/70.2; 424/93.3; 935/93; 935/96; 935/106

[58] Field of Search .............. 424/93.21, 93.3, 424/93.7; 435/42, 69.1, 70.2, 240.21, 240.26, 172.2; 935/93, 96, 106

[56] References Cited

PUBLICATIONS

Buerstedde et al. (1990). EMBO J. vol. 9 No. 3, 921–927.
Takeda et al. (1992) Proc. Natl. Acad. Sci. OSA vol. 89, 4023–4027.
Kao, F–5. (1973) Proc. Natl. Acad. Sci. USA vol. 73, 2893–2898.
Epner et al (1992) Current Biology vol. 2 No. 5, 262–264.
Capecchi, *Trends in Genetics* 5: 70–76, 1989.
Capecchi, *Science* 244: 1288–1292, 1989.
Brenner et al., *Mol. Cell. Biol.* 5: 684–691, 1985.
Finn et al., *Mol. Cell. Biol.* 9: 4009–4017, 1989.
Fournier and Ruddle, *Proc. Natl. Acad. Sci. USA* 74: 319–323, 1977.
Fournier, *Proc. Natl. Acad. Sci. USA* 78: 6349–6353, 1981.
Fournier and Frelinger, *Mol. Cell. Biol.* 2: 526–534, 1982.
Anthwal et al., *Som. Cell Mol. Genet.* 11: 177–187, 1985.
Saxon et al., *Mol. Cell. Biol.* 5: 140–146, 1985.
Tunnacliffe et al., *EMBO J.* 2: 1577–1584, 1983.
Lugo et al., *Mol. Cell. Biol.* 7: 2814–2820, 1987.
Shapero et al., *Som. Cell Mol. Genet.* 20: 215–213, 1991.
Buerstedde and Takeda, *Cell* 67: 179–188, 1991.
Baba and Humphries, *Virology* 135: 181–188, 1984.
Baba et al., *Virology* 144: 139–151, 1985.

*Primary Examiner*—Robert D. Budens
*Assistant Examiner*—Julie E. Reeves
*Attorney, Agent, or Firm*—Christensen O'Connor Johnson & Kindness PLLC

[57] ABSTRACT

An avian/mammalian microcell hybrid immortalized pre B cell line containing a mammalian chromosome that carries a selectable marker has been produced. The avian/mammalian microcell hybrid immortalized pre B cell line can be used for introducing predetermined point mutations into specific mammalian chromosomal loci via high frequency homologous recombination.

1 Claim, No Drawings

RECOMBINATION-PROFICIENT AVIAN/MAMMALIAN MICROCELL HYBRIDS

This invention was made with government support under grants DK44746 and HL48356 awarded by the National Institutes of Health and grant GM26449 awarded by the National Institute of General Medical Sciences. The government has certain rights in the invention.

1. Field of the Invention

This invention relates to the field of genetic engineering and provides a convenient biological system for introducing predetermined mutations into specific mammalian chromosomal loci via high-frequency homologous recombination.

2. Background of the Invention

The ability to specifically modify a genetic locus by homologous recombination has become a valuable tool in the study of gene function. Most gene targeting experiments have been done in mouse embryonic stem (ES) cells, providing a means of systematically generating strains of mice carrying predetermined mutations. In addition, somatic tissue culture cells have been used to target genetic loci where many biologic questions can be answered directly and swiftly. However, these experiments have been hampered by the fact that mammalian cells integrate exogenous DNA into random chromosomal positions much more frequently than into the homologous gene locus. Several experimental approaches, such as positive-negative selection, sib-selection using polymerase chain reaction (PCR), and promoter or enhancer traps, have been devised to isolate rare homologous recombinants. However, the most effective of these approaches, the promoter trap, is not feasible when either the gene being analyzed is not expressed or a regulatory region is being targeted.

Chickens generate antibody diversity by two mechanisms: following rearrangement of the single V and J gene segments by site-specific V(D)J recombination, chicken B cell progenitors migrate into the bursa and continue diversification of the arranged V segment by a gene conversion event. Avian leukosis virus (ALV) induces B cell tumors in the bursa which seem to be arrested at this developmental stage. Furthermore, cell lines derived from these tumors exhibit the same diversification phenotype. Recently, Buerstedde and Takeda reported that transfection of these chicken B cell lines results predominantly in homologous recombination between transfected chicken DNA and the corresponding chromosomal alleles. High targeting frequencies, >80%, were obtained for multiple chicken loci and transcriptional activity of the target locus does not appear to be required. Other groups have reported similar targeting frequencies, which are orders of magnitude higher than those reported for mammalian cells.

SUMMARY OF THE INVENTION

The invention provides a hybrid immortalized avian pre B cell line containing a mammalian chromosome. Such simple hybrid cell systems are useful for introducing predetermined mutations into specific mammalian chromosomal loci via high-frequency homologous recombination. The invention is described in terms of construction and use of a representative hybrid arian leukosis virus transformed chicken pre B cell line containing a human chromosome 11 (ATCC No. CRL 11866).

DETAILED DESCRIPTION OF THE PREFERRED EMBODIMENT

We have exploited the ability of immortalized chicken pre B cells to undergo high frequency homologous recombination to develop a general method for efficient mutational analysis of mammalian and particularly human chromosomal loci by homologous recombination. A human chromosome containing the locus of interest and a selectable marker gene is transferred into exemplary DT40 cells by microcell mediated fusion. The targeted mutations in the locus of interest are isolated at high frequency in the DT40/human microcell hybrids, followed by transfer of the targeted chromosome into a cell line where direct phenotypic analysis can be assessed.

The somatic cell genetic aspects of this experiment were non-trivial. Inter-class crosses are inefficient, and chicken/human whole-cell hybrids were known to be extremely unstable (Kao et al., *Proc. Natl. Acad. Sci.* 70:2898, 1973).

We optimized conditions for producing chicken/human microcell hybrids, which we obtained at frequencies of $\approx 10^{-6}$, and found that individual microcell hybrid clones were surprisingly stable. Most of the chicken/human microcell hybrids contained an intact human chromosome, and the donor chromosome was stably maintained under selective conditions. Importantly, these hybrids retained their capacity for high frequency homologous recumbination. Recombination of a promoter-containing substrate into the chicken ovalbumin locus occurred in 24 of 29 transfectants tested, similar to parental DT40 cells. Moreover, homologous insertions of promoter-containing neo constructs into the human β-globin and cHras loci on chromosome 11 occurred at frequencies of 10–20%. These frequencies have not yet been optimized. Therefore, this hybrid cell system allows the efficient modification of human chromosomal alleles. Finally, we developed methods for transferring the modified human chromosomes from DT40-microcell hybrids back to mammalian cells. A representative transfer cycle for human chromosome 11 is described below: from a mouse cell background to chicken DT40 cells and back into murine cells. This system permits a systematic analysis of specific human loci that have been modified by homologous recombination.

Key features of this approach are: (i) The targeted alleles are non-essential in the cells in which the modifications are produced. (ii) Recombination frequencies of 10–20% can be obtained without optimization or enrichment. (iii) Both expressed and non-expressed genes can be modified efficiently. (iv) Function is assessed in a separate experiment in which the modified chromosomes are transferred to various mammalian cell types.

The following terms are used to describe the invention:

A "hybrid cell line" contains genetic material from two different parental cells.

The term "immortalized" refers to cells that are capable of indefinite growth in vitro.

The term "containing" refers to genetic material located within the nucleus of a cell.

"Avian cell" means a bird cell, preferably that of a chicken or other domesticated bird.

"Pre B cell lines" are immortalized cells derived from the B-cell lineage. Cells from the B-cell lineage have characteristic B-cell properties which may include B-cell surface markers and/or B-cell specific enzymes such as the RAG2 gene product.

"Mammalian chromosome" refers to whole chromosome(s) or chromosome fragment(s). Chromosome fragments encompass pieces of chromosomes of any size. Such a chromosome or chromosome fragment typically contains a predetermined locus for homologous recombination. Chromosome fragments may be obtained by exposing donor cells to treatments that cause chromosome breaks such as exposure to gamma irradiation. Alternatively, chromosome fragments may be obtained during the colcemid treatment that causes micronuclei formation. Prolonged treatment with colcemid increased the frequency of chromosome fragments included in the micronuclei.

In this study, we have used human chromosome 11 as a model system. The human β-globin locus, located at 11 p 15, is comprised of five linked functional β-like globin genes. These genes are arrayed on the chromosome in the order in which they are expressed developmentally. The human β-globin locus control region (LCR), located 6–22 kb upstream of the human ε-globin gene, is now recognized as a regulatory domain that controls the chromatin structure, replication timing, and transcription of the entire β-globin domain. The LCR is operationally defined by five DNase I hypersensitive sites (for a review, see: Epner et al., *Current Biology* 2:262–264, 1992). Since we were interested in understanding how such regulatory regions function in mammalian gene regulation, this is the region on human chromosome 11 we chose to target. Previous attempts to target this locus had met with limited success. These prior experiments involved targeting a human chromosome 11 in mouse erythroleukemia cell (MEL) hybrids containing a normal human chromosome 11 (N-MEL). We estimate the overall targeting frequency in the N-MEL hybrids to be between $10^{-8}$ and $10^{-9}$. Such low targeting frequencies make this type of mutational analysis impractical.

We show here that we can transfer an intact human chromosome into DT40 cells, efficiently modify human chromosomal loci, and then transfer the altered human chromosome out of DT40 cells and into a cell line where direct phenotypic analysis of the introduced mutations can be carried out.

The introduction of limited numbers of chromosomes from one cell to another is well established in the literature (see, for example: Fournier and Ruddle, *Proc. Natl. Acad. Sci.* 74:319–323, 1977; Fournier, *Proc. Natl. Acad. Sci.* 78:6349–6353, 1981; which are incorporated by reference herein in their entirety). These methods rely on the generation of small cell-like structures, termed microcells, containing a limited amount of genetic material within a micronucleus that is itself surrounded by a rim of cytoplasm and an intact plasma membrane. Microcells provide an efficient vector for transferring chromosomes into recipient cells using cell fusion methods. The donor chromosomes are typically marked to facilitate selective retention of specific donor chromosome(s) in the resulting microcell hybrids. Suitable selectable markers for mammalian and avian cells are well known and include the *E. coli* gpt gene (confers xanthine-aminopterin-thymidine resistance), the neomycin resistance gene (neo) from transposon Tn5 (confers G418 resistance), the hygromycin phosphotransferase gene (confers resistance to hygromycin B), the herpes simplex virus type 1 (HSV) thymidine kinase (tk) gene (complements TK⁻cells and confers hypoxanthine-aminopterin-thymidine (HAT) resistance), the hypoxanthine phoshoribosyltransferase (HPRT) gene (complements HPRT⁻cells and confers HAT resistance), and the adenine phosphoribosyltransferase (APRT) gene (complements APRT⁻cells and confers adenine-aminopterin-thymidine (AAT) resistance).

Chromosomes may be marked with selectable markers by integration in a number of well established ways (see, for example: Fournier and Frelinger, *Mol. Cell. Biol.* 2:526–534, 1982; Athwal et al., *Som. Cell. Mol. Genet.* 11:177–187, 1985; Saxon et al., *Mol. Cell. Biol.* 5:140–146, 1985; Tunnacliffe et al., *EMBO J.* 9:1577–1584, 1983, and Lugo et al., *Mol. Cell. Biol.* 7:2814–2820, 1987; which are incorporated by reference herein in their entirety). These methods rely on random integration events to insert marker genes into the chromosomes of the host cell. Certain of these methods, such as defined translocations (Fournier and Frelinger, ibid.) and calcium phosphate mediated coprecipitation (Saxon et al., ibid.), are limited due to a low number of suitable translocations or a low frequency of gene transfer, respectively. Retroviral vectors provide an efficient means of effecting gene transfer that permit the recovery of a large number of integration events from a single infection (Lugo et al., ibid.). Retroviral vectors integrate into chromosomes quasirandomly, and the integrated vector sequence has precisely defined ends that facilitate analysis of the insertion site. A packaging cell line is typically employed to produce defective retrovirus free of intact helper virus. An exemplary defective retrovirus is ZIP-Neo SV(X)I (Cepko et al., *Cell* 37:1053–1062, 1984; which is incorporated by reference herein in its entirety) which may be employed with the packaging cell line ψ-AM (Cone and Mulligan, *Proc. Natl. Acad. Sci.* 78:6349–6353, 1984). Alternatively, plasmids containing expression units capable of directing the expression of selectable marker genes may be electroporated into cells using, for example, a Bio-Rad Gene Pulser™ apparatus to transfect linear plasmids into suitable recipient cells. One suitable vector for this purpose is the tgCMV/HyTk plasmid (Lupton et al., *Mol. Cell. Biol.* 7:2814–2820, 1987; which is incorporated by reference herein in its entirety) which confers hygromycin resistance to the recipient cell. The plasmid also complements TK⁻cells. Plasmid tgCMV/HyTk contains an in-frame fusion between the hygromycin phosphotransferase gene and the herpes simplex virus type I thymidine kinase under the control of the human cytomegalovirus IE4 promoter.

Human primary diploid fibroblasts are preferrably used as the source of the human chromosomes. Primary fibroblasts are free of the chromosome abnormalities documented in malignant cells. An exemplary source of diploid fibroblasts, is from human foreskin. Such primary fibroblasts are used at a very early passage to capitalize on the capacity of the cells to form micronuclei. Primary cells are preferably used at or before passage 10. For adherent donor cells, the cells are preferably grown on a solid support, such as a plastic disc or "bullet" as described by Fournier and Ruddle (ibid.) and Lugo (ibid.).

As noted above, methods for producing microcell hybrids are well established in the literature. Microcells are produced from donor cells (preferably from primary human diploid fibroblasts that have selectable marker genes integrated into the chromosomes) by first exposing the cells to high concentrations of a mitotic inhibitor, such as colcemid for between 24 and 48 hours, at a concentration between .01 and 10 μ/ml. Exposure to the colcemid induces the cells to form micronuclei. The size of the micronuclei will determine the amount of genetic information available for transfer during microcell hybridization. After micronuclei have formed, the cells are enucleated by centrifugation in the presence of 5 to 20 μg/ml cytochalasin B in an appropriately buffered solution such as serum-free growth medium of phosphate-buffered saline (PBS). Enucleation of adherent cells is achieved by centrifuging the cells grown on a solid support, such that the supports are positioned vertically in centrifuge tubes containing the cytochalasin B solution. Non-adherent cells are enucleated by centrifugation through a percoil gradient containing cytochalasin B, as described in more detail below. The micronuclei are recovered from the resulting pellet. The micronuclei are preferably size selected to remove whole cells and to isolate micronuclei that contain approximately one chromosome. Size selection may be accomplished using sequential filtration through 8- and 5-µm filters (Shapero, Langston and Fournier, *Som. Cell. Mol. Gen.* 20:215–231, 1994; which is incorporated by reference herein in its entirety). Alternatively, micronuclei can be size separated by unit gravity sedimentation on a linear 1–3% bovine serum albumin gradient, taking the upper fraction containing the smaller micronuclei as described by Fournier and Ruddle (ibid.).

Fusion of the donor microcells to a suitable recipient cell has been described in detail by, for example, Fournier and Ruddle (ibid.). Suitable cells for use in the present invention for targeted integration include immortalized avian cells which exhibit a high level of homologous recombination, such as LSCC-DT40 and LSCC-RP9. Avian cells may be immortalized using a number of techniques well established in the literature including viral transformation using, for example, avian reticuloendotheliosis virus, Marek's disease virus, and chicken syncitial virus. Chicken pre-B cells immortalized with avian leukosis virus, for example, have been shown to have a high level of homologous recombination (Buerstedde and Takeda, *Cell* 67:179–188, 1991; which is incorporated herein by reference in its entirety). Immortalized avian pre-B cells may be obtained, for example, by the methods described by Baba and Humphries (*Virology* 135:181–188, 1984; which is incorporated herein by reference in its entirety) and Baba et al. (*Virology* 144:139–151, 1985; which is incorporated herein by reference in its entirety). Briefly, day-old susceptible chickens are infected by intravenous injection with an avian leukosis virus. Cell suspensions prepared from bursal lymphoma tumors of infected chicks are used to infect syngeneic chicks. Cell lines are obtained from the bursal lymphoma tumors of the transferable tumors. A preferred immortalized pre-B cell line is LSCC-DT40 (Baba et al., ibid.). An exemplary method for identifying cells with increased rates of homologous recombination is described by Buerstedde and Takeda (Cell: 67:179–188, 1991, which is incorporated by reference herein in its entirety).

In instances in which modified mammalian chromosomes are to be transferred from donor avian cells into recipient mammalian cells, suitable mammalian cells may be chosen from a wide variety of known cell lines including MEL cells, mouse 3T6 cells, and the like, or any mammalian cell type that can be grown in vitro. The choice of cell line would be evident to one skilled in the art given the selectable markers present in the mammalian chromosome(s). In this regard, the choice of the cell type of the recipient may be of importance when expression of the target gene is required. In cases where gene expression from the native regulatory sequences is required, it is preferable to use recipient cells of a cell type that normally expresses the gene of interest. Mouse erythroleukemia (MEL) cells, for example, are useful in studying the expression of erythroid cell gene products such as the globin genes. To fuse the microcells with the recipient cells, the preparation of microcells is incubated with the recipient cells for 10 to 15 minutes at 37° C. In the case of adherent cells, the microcells are preferably suspended in a solution of 100–200 µg/ml of phytohemagglutinin P and applied to monolayers of recipient cells to allow for agglutination. In the case of non-adherent recipient cells, the microcells and recipient cells are suspended together in a test tube. The microcells are fused to the recipient cells by a sixty second exposure of between 44 to 50% (wt/wt) polyethylene glycol (mW 1300–1600). The microcell hybrids are allowed to incubate overnight in nonselective medium The cells are then placed under selection in the appropriate medium to select for the presence of cells containing chromosome(s) from the donor cell having an integrated selectable marker gene.

The presence and identification of donor chromosomes in the microcell hybrids may be carried out using any number of well established methods. In the case of microcell hybrids containing human chromosomes, human chromosomes may be detected by, for example, filter hybridization to detect human alleles or DNA markers. Representative human alleles include argininosuccinate synthetase, adenosine deaminase, nucleoside phosphorylase, and insulin, and representative arbitrary DNA markers include G8, 3.6/1.2, pAW101, p267, D20S2, and D7S8 (Lugo et al., ibid.). FISH karyotyping (Trask et al., *Am. J. Hum. Genet.* 48:1–15, 1991, and Brandiff et al., *Genomics* 10:75–82, 1991; which are incorporated herein in their entirety) may be used to identify the presence of donor genomic DNA, as described in more detail below.

Pursuant to the present invention, donor mammalian chromosomes can be conveniently and efficiently modified by homologous recombination in the recipient avian pre-B cell line. Such chromosomal modifications include insertion of regulatory and/or coding sequences, deletion of one or more nucleotides, and replacement of one or more native nucleotides that may result in a change in amino acid codon(s). Modifications may include replacement of promoter regions, insertion of upstream activation sequences, insertion of targeting signals such as secretory signals, modifications in amino acid sequences that increase or decrease the activity of the resulting protein, and insertion of high affinity binding regions (especially with respect to immunoglobulins and cell surface receptors). Modified nucleic acid sequences may be prepared using common techniques well established in the art and include restriction digest and ligation, PCR mutagenesis, and chemical synthesis of suitable oligonucleotides. Modified sequences according to the invention are flanked by regions of homology. These regions of homology are typically asymmetrical such that one flanking region is shorter than the other to facilitate genomic targeting. Requirements for minimal lengths for flanking sequences have been determined in systems in which the frequency of homologous recombination is very low. In this regard, flanking sequences used for mammalian homologous recombination require at least 500 bp of homologous flanking sequence for detectable occurrence of a homologous recombination event (Scheerer and Adair, *Mol. Cell. Biol.* 14:6664–6673, 1994). Typically, targeting sequences contain a total of 5–10 kb of homologous sequences with at least 1 kb of the sequence in the short flanking region. The minimum length of homologous flanking region required in the highly efficient system of the present invention may be shorter than the sequences required for mammalian systems. It would be evident to one skilled in the art to apply the knowledge established in the literature (for example, Scheerer and Adair, ibid.) to determine the minimum length of homologous flanking region required for homologous recombination in the subject hybrid avian/mammalian cells. The identification of clones that have undergone a desirable homologous recombination event may be confirmed by Southern analysis of the genomic DNA of such clones.

It may be preferable to include a selectable marker within the targeting nucleotide sequence to facilitate identification of successful integration events. The choice of a suitable selectable marker would be evident to one skilled in the art.

Considerations in selecting a suitable selectable marker include, but are not limited to, the genotype of the recipient cell and the presence of other selectable markers on the chromosome. Suitable selectable markers include those discussed above. It may be preferable to remove the selectable marker either before or after the chromosome has been transferred to the appropriate recipient cell. An exemplary method for the precise deletion of such sequences is described by Fiering et al. (*Proc. Natl. Acad. Sci.* 90:8469–8473, 1993; which is incorporated by reference herein in its entirety). Briefly, the 48 bp FRT yeast recombination sites are used to flank the selectable marker gene. Precise deletion of the selectable marker sequence is achieved by transfection of the cells with expression vectors capable of expressing the yeast FLP recombinase.

The invention is further described in the following Examples, wherein: Examples 1–3 describe construction of mouse microcell hybrids containing human chromosome 11; Example 4 describes production of chicken/human hybrids containing human chromosome 11; Example 5–7 describe targeted integration into the chicken or human genome in the chicken/human microcell hybrids; and Example 8 describes construction of mouse microcell hybrids containing human chromosome 11 donated from a chicken/human microcell hybrid. An appended Methods section discusses karyotype analysis and nucleic acid isolation and blot hybridization protocols.

EXAMPLE 1

Construction of F(Nht)317 donor rat hepatoma microcell hybrid cells

A donor cell line carrying a human chromosome 11, designated F(Nht)317, was constructed essentially as described by Shapero, Langston and Fournier (ibid.). Briefly, human chromosomes were marked with plasmid tgCMV/HyTk, which contains an in-frame fusion between the hygromycin phosphotransferase gene and the herpes simplex virus type I thymidine kinase under the control of the human cytomegalovirus IE4 promoter (Lupton et al., *Mol. Cell. Biol.* 7:2814–2820, 1987; which is incorporated by reference herein in its entirety), by transfection with the Bam HI-linearized plasmid.

Primary diploid human fibroblasts, HDF 1–85 cells, were used as the source of human chromosomes. The fibroblasts were propagated in a medium containing a 1:1 mixture of Dulbecco's modified Eagle's medium and Ham's F12 medium supplemented with 10% fetal calf serum. Approximately 108 exponentially growing HDF 1–85 cells were trypsinized and suspended to $1.2 \times 10^7$ cells/ml in ice-cold phosphate-buffered saline (PBS). The Bam HI-linearized tgCMV/HyTk plasmid was added to the cells at 10 µg/ml. The cells were electroporated at 20 µF, 2000 V using a Bio-Rad GenePulser. The transfected cells were plated in nonselective medium for 48 hours. After growth in nonselective medium, 500 µg/ml hygromycin B was added to select for the presence of inserted plasmid. After 21 days, three pools, each containing approximately 350 independent transfectants, were designated HDF-ht A, B, and C.

The transfectant pools were each grown on plastic bullets cut from tissue culture dishes. The cells were micronucleated by incubation in the presence of 10 µg/ml colcemid for forty-eight hours. After incubation the cells were enucleated by centrifuging the bullets in 10 µg/ml cytochalasin B in serum-free growth medium (Fournier and Ruddle, ibid.). The bullets were centrifuged at 39,000×g for 35 minutes at 28° or 32° C. to enucleate the cells. After centrifugation, the isolated microcells were resuspended in serum-free medium and filtered sequentially through 8- and 5-µm filters. Particles were collected by centrifugation, resuspended in 1 ml serum-free medium, and added to a 70–80% confluent monolayer of FAO-1 rat hepatoma recipient cells in a 25-cm$^2$ flask. The FAO-1 cell line (Killary and Fournier, *Cell* 11 38: 523–534, 1984 ) is a hypo xanthine-guanine phosphoribosyltransferase-deficient (HPRT$^-$), ouabain-resistant (Oua$^r$) rat hepatoma line derived from H4IIEC3. One milliliter of serum-free medium containing 200 µg/ml of phytohemagglutinin P was added to the cells. After 20 minutes of incubation at 37° C. to permit agglutination, the cells and microcells were fused by a one minute exposure of 50% (wt/wt) polyethylene glycol 1500. After an overnight incubation in nonselective medium, the recipient cells were plated in medium containing 3 µM ouabain and 500 µg/ml hygromycin B to select against unfused donor and recipient cells. Individual colonies were picked using glass cloning rings. One hundred and ninety-one independent hybrid clones, each potentially containing a different HyTk-marked human chromosome, were isolated. The genotypic complexity of 10 randomly chosen hybrids was assessed by fluorescence in situ hybridization (FISH; see Methods below). These hybrids, which were designated F(Nht) series clones, typically contained one or two human chromosomes. One clone, F(Nht)317, was shown to contain a human chromosome 11 marked with HyTk and an unmarked human chromosome 14. F(Nht)317 cells were maintained in 1:1 Ham's F12:Dulbecco's Modified Eagle's Medium with 10% fetal bovine serum (6Gibco/BRL) in the presence of 500 µg/ml hygromycin B.

EXAMPLE 2

Construction of mouse microcell hybrid clone M(h11)1 containing human chromosome 11

Human chromosome 11 was recovered by micronucleation from donor F(Nht)317 rat hepatoma microcell hybrid cells (HPRT$^-$, Hm$^r$). Donor F(Nht)317 cells were grown in the presence of 500 µg/ml hygromycin B. Microcells were produced by incubating the cells in 0.5 µg/ml colcemid for 48 hours. The cells were allowed to attach to plastic bullets followed by centrifugation in the presence of 10 µg/ml cytochalasin B, as previously described (Shapero, Langston and Fournier, ibid.). After centrifugation, the isolated microcells were resuspended in serum-free medium and filtered through 8- and 5-µm filters. MEL cells were maintained in Dulbecco's Modified Eagle's Medium with 10% calf bovine serum (CBS, Hyclone). Microcells were collected by centrifugation, resuspended in 1 ml of serum-free medium, and mixed in a 50 ml sterile disposable polypropylene tube (Corning Inc., Corning, N.Y.) with $10^7$ MEL (APRT$^-$, Hm$^s$) recipient cells in 1 ml of serum-free medium. After a 10 minute incubation at room temperature, the cell/microcell suspension was pelleted by centrifugation and fused by a one minute exposure to 50% (wt/wt) polyethylene glycol 1500 (NBS Biologicals, Haverhill, Suffolk, England). Hybrid clones were selected in 20 µg/ml 2,6-diaminopurine (DAP) plus 500 µg/ml hygromycin B (Boehringer Mannheim, Indianapolis, Ind.). One clone, M(h11)1, was picked and genotyped to determine whether human chromosome 11 was retained. Fluorescence in situ hybridization (FISH) using total human DNA as a probe demonstrated that a single, intact human chromosome 11 was present. M(h 11)1 was maintained in Dulbecco's Modified Eagle's Medium with 10% calf bovine serum and containing 250 µg/ml hygromycin B.

EXAMPLE 3

Construction of mouse whole cell hybrid HR9 containing human chromosome 11

HR9, derived from N-MEL, contains a $Hm^r$ gene homologously inserted into the human β-globin locus located at 11 p 15. N-MEL is a mouse erythroleukemia hybrid retaining 3–4 human chromosomes including a single copy of human chromosome 11. This line was generated by fusing EBV-transformed human lymphocytes with MEL (APRT$^-$) cells (Deisseroth and Hendrick., Cell 15:55–63, 1978). MEL/human hybrids retaining human chromosome 11 were isolated by panning with an antibody directed towards a constitutively expressed surface antigen encoded by a gene on human chromosome 11 (Forrester et al., Genes & Dev. 4:1637–1649, 1990). The human chromosome 11 in N-MEL was modified to contain a hygromycin (Hm) phosphotransferase gene driven by the Friend virus long terminal repeat enhancer/promoter (F-LTR) in the locus control region (LCR) of the human β-globin locus, located by a rare homologous insertion at 11 p 15 (Kim et al., Genes & Dev. 6:928–938, 1992). The homologous recombinant HR9 was karyotyped using FISH to confirm the presence of an intact human chromosome 11. HR9 cells were maintained in Dulbecco's Modified Eagle's Medium supplemented with 10% calf bovine serum and 250 µg/ml hygromycin B.

EXAMPLE 4

Production of chicken/human microcell hybrids containing human chromosome 11

As reported in the literature, the immortalized chicken pre-B cell line LSCC-DT40 (DT40) was induced by a intravenous viral infection of one-day old chicks of the susceptible Hyline SC chicken line (Hyline International, Dallas Center, Iowa) with $2 \times 10^5$ IU of the avian leukosis virus Rous-associated virus-1 (ATCC VR334) that was obtained from a single pooled source of biologically cloned virus (Baba and Humphries, ibid.; and Baba et al., ibid). Cell suspensions were prepared from individual primary or metastatic bursal lymphoma tumors. The suspensions were transferred intravenously into young syngeneic recipient chickens. Cell suspensions were prepared from these transplantable bursal lymphoma tumors. The cell suspensions were transferred into a second set of young syngeneic recipient chickens. Cell suspensions prepared from the transplantable tumors were cultured in vitro in modified Hahn's medium containing $5 \times 10^{-5}$ M/ml 2-mercaptoethanol (Hahn et al., J. Natl. Cancer Inst. 59:267–271, 1977; which is incorporated by reference herein in its entirety). The cell line LSCC-DT40 was cultured from a bursal lymphoma tumor obtained after the second in vivo transfer.

In the present experiments, chicken microcell hybrids derived from donor cells HR9 and M(h11)1 were isolated by first growing 500 ml spinner cultures in 1 liter flasks of donor HR9 or M(h11)1 hybrid cells. The cells were micronucleated in 0.1 µg/ml colcemid for 24 hours followed by enucleation via centrifugation through Percoll (Pharmacia, Piscataway, N.J.) in the presence of 20 µg/ml cytochalasin B (as described in Stubblefield and Pershouse, Som. Cell. and Mol. Genetics 18:485–491, 1992; which is incorporated by reference herein in its entirety). Approximately twenty million cells were loaded on each of eight gradients for each fusion. The gradients were centrifuged at 20,500 rpm in a Beckman L8-M ultracentfifuge using a type 70Ti rotor for 80 minutes at 32° C. After centrifugation, the gradient material from approximately 2 cm below the top down to the region just above the Percoll pellet was collected from each gradient and pooled. The collected, pooled gradient material was centrifuged at 800–1000 g for 10 minutes. The supernatant was discarded, and the particle pellet was rinsed with serum-free media and centrifuged at least three times to remove the Percoil. After the centrifugation, the isolated microcells were resuspended in serum-free medium and filtered sequentially through 8- and 5-µm filters. Particles were collected by centrifugation and resuspended in 1 ml serum-free medium. The resulting microcells were fused to 1 ml of approximately $2-3 \times 10^7$ recipient DT40 cells (APRT$^+$, Hm$^s$) in a 50 ml sterile, disposable polypropylene tube (Corning Inc., Corning, N.Y.). After a 10 minute incubation at room temperature, the cell/microcell suspension was pelleted by centrifugation and fused by a one minute exposure to 50% (wt/wt) polyethylene glycol 1500 (NBS Biologicals, Haverhill, Suffolk, England). The fusions were incubated as a pool in non-selective medium for 24 hours, then plated at clonal density into 8×96-well microtiter plates containing 0.2 ml/well of medium containing adenine-aminopterinthymidine (AAT) plus 2 mg/ml hygromycin B. After 3–4 weeks, hybrid clones were picked individually and maintained in medium containing 0.5 mg/ml hygromycin B. Microcell hybrids derived from HR9 donors are designated D(HR9) series clones, and those derived from M(h11)1 donors are designated D(Mh11) series clones. D(Mh11) and D(HR9) cells were grown in Dulbecco's Modified Eagle's Medium with 10% calf bovine serum (CBS, Hyclone), 10% tryprone phosphate buffer, 1% chicken serum (GIBCO/BRL, Gaithersburg, Md.) and 250 µg/ml hygromycin B supplemented with 500 µg/ml hygromycin B.

One representative hybrid from each cross was chosen for further analysis. D(HR9)6 was subcloned to ensure a clonal population. Two hybrid subclones, D(HR9)6-8 and D(HR9)6-26, were chosen for further analysis to assess clonal variation of the recombinant-proficient phenotype. The genotypes of D(Mh1 1)1, D(HR9)6-8, and D(HR9)6-26 were determined by FISH. A probe derived from total human DNA hybridized to metaphase spreads and revealed that both hybrids retain a single, apparently intact, human chromosome 11. The identification of the human chromosome in the DT40 microcell hybrids was confirmed by PCR marker analysis using primers to three human chromosome 11 markers: CAT at 11p13, CLG at 11 q21–22 (Theune et al., Genomics 9:511–516, 1991), and HBB at 11 p15 (Kim et al., Genes & Dev. 6:928–938, 1992). The mouse repetitive DNA sequence RI/RII (Gebhard and Zachan, J. Mol. Biol. 157:453–471, 1982) was used as a probe to determine whether, in addition to the human chromosome, any mouse DNA had been transferred. FISH results indicated that no mouse DNA was present in either series of hybrids. The human chromosome was stably maintained under selective conditions in the hybrids, which have been maintained in continuous culture for more than 6 months without any appreciable loss of the human chromosome (<1% as determined by FISH). To determine whether the targeting locus, the human β-globin locus, was intact in the hybrids, Southern blot analysis was performed using six different probes spanning approximately 200 kilobases (kb) of the human β-globin locus. Results confirmed that the human β-globin locus was intact in the D(Mh11)1, D(HR9)6-8, and D(HR9)6-26 hybrids. These results demonstrated the ability to transfer human chromosome 11 into DT40 cells and, furthermore, the chromosome appeared intact and was maintained under selective conditions.

The representative cell line D(Mh11)1 was deposited on Mar. 30, 1995, as accession number CRL11866 at the American Type Culture Collection, 12301 Parklawn Drive, Rockville, Md. 20852 U.S.A.

EXAMPLE 5

Targeted integration into the chicken ovalbumin locus in DT40/human microcell hybrids To determine whether the presence of a human chromosome in DT40 cells affects the efficiency of homologous recombination, the chicken ovalbumin gene targeting construct used by Buerstedde and Takeda (Cell 67:179–188, 1991; which is incorporated by reference herein in its entirety) was transfected into the D(Mh1 1 )1, D(HR9)6-8, and D(HR9)6-26 hybrids. This ovalbumin targeting construct was made by cloning the 3.2 kb and 4.8 kb HindIII chicken ovalbumin gene fragments from the plasmid pOV12 (Lai and Woo, *Proc. Natl. Acad Sci.* 77:244–248, 1980) upstream and downstream of a neomycin phosphotransferase gene (neo$^r$) driven by the chicken beta actin promoter. Briefly, exponentially growing cells were harvested and suspended to $1.25 \times 10^7$ cells/ml of serum-free Dulbecco's Modified Eagle's Medium. Twenty-five micrograms of BamHI-linearized ovalbumin gene construct plasmid DNA was added. The cells were electroporated at 25 µF and 550 volts, using a Bio-Rad Gene Pulser™ apparatus. The transfected cells were incubated as a pool in nonselective medium for 24 hours, then plated into 4×96-well microtiter plates in DT40-conditioned medium containing 2.5 mg/ml G418 (Gibco/BRL). After 2 weeks, clones were picked individually and expanded. A typical transfection yielded 10–15 clones per 96-well microtiter plate: therefore, each clone picked represents an independent transfection event.

Genomic DNA from randomly chosen G418-resistant transfectants digested with ScaI was analyzed by Southern blotting and hybridization with junction and neo$^r$probes (see Methods below). A correct targeting event yields an approximately 15 kb fragment with both probes. A non-homologous insertion yields a wild type 12.8 kb fragment only with the junction probe. In a representative sample of seven randomly chosen clones, 6 of 7 clones contained a targeted insertion. In addition to the new 15 kb fragment, all of the recombinants exhibited hybridization to the wild type 12.8 kb fragment, indicating that DT40 contains at least two ovalbumin alleles. The homologous recombination frequencies for each of the hybrids are shown in Table 1 (see below). These frequencies are similar to those of the parental DT40 cells, indicating that the hybrids retain their capacity for high frequency homologous recombination.

EXAMPLE 6

Targeted integration into the human β-globin locus in DT40/human microcells hybrids To determine whether the DT40/human microcell hybrids could be efficiently used to modify human chromosomes, the DMh11)1, D(HR9)6-8 and D(HR9)6-26 hybrids were transfected with a targeting vector, p5'εFneo, which was designed to insert a neo$^r$ gene into the human β-globin LCR. The p5'εFneoF/tk targeting construct contained a 9 kb EcoRI/BamHI human β-globin LCR gene fragment with a neo gene driven by the F-LTR inserted at a unique HpaI site between hypersensitive sites I and II of the LCR. This vector contains a Friend virus long terminal repeat promoter/enhancer (F-LTR)-driven neo$^r$ gene at a unique HpaI site approximately 7.5 kb upstream the s-globin gene between 5' hypersensitive sites (HS) 1 and 2 of the LCR. One feature of this construct is that the F-LTR/neo$^r$ sequences are flanked by single copies of the 48-bp FLP recombinase target (FRT) sites, allowing FLP-mediated deletion of the selectable marker gene. Exponentially growing cells (DMh11)1, D(HR9)6-8 and D(HR9)6-26) were each harvested and suspended to $1.25 \times 10^7$ cells per ml of serum-free Dulbecco's Modified Eagle's Medium. Twenty-five micrograms of ApaLI-linearized p5'ε FneoF/tk plasmid DNA was added, and the cells were electroporated at 25 µF and 550 volts, using a Bio-Rad Gene Pulser™ apparatus. The cells were incubated as a pool in nonselective medium for 24 hours, then plated into 4×96-well microtiter plates in DT40-conditioned medium containing 2.5 mg/ml G418 (Gibco/BRL). After 2 weeks, clones were picked individually and expanded. A typical transfection yielded 10–15 clones per 96-well microtiler plate: therefore, each clone represents an independent transfection event. BglII digested genomic DNA from randomly chosen G418-resistant DMh11)1 clones was analyzed by Southern blotting using the junction and neo$^r$probes. One of the clones was designated D(Fneo)5. A correct targeting event yields a 10 kb fragment with both probes. A non-homologous insertion yields a 7.7 kb wild-type fragment with the junction probe, but not with the neo$^r$ probe. As shown in Table 1, the targeting frequency of DMh11)1 using this vector is 13.9%.

TABLE 1

| Frequency of homologous recombination in DT40(hsall) microcell hybrids. | | | |
|---|---|---|---|
| Microcell Hybrid | HR Constructs[a] | HR frequency (%)[b] | |
| D(Mh11)1 | cOVneo | 12/12 | (100) |
|  | p5'εFneo | 5/36 | (13.9) |
| D(HR9)6-8 | cOVneo | 3/5 | (60) |
|  | p5'εFneo | 3/26 | (11.5) |
| D(HR9)6-26 | cOVneo | 9/12 | (75) |
|  | p5'εFneo | 0/13 | (0) |
| D(Fneo)5 | HrasPGKHygro | 3/15 | (20) |

[a]HR = homologous recombination
[b]number of homologous insertions/number of G481 resistant clones analyzed Targeted insertion of the p5'ε Fneo$^r$ vector in the D(HR9) series hybrids results in replacement of a hygro$^r$ gene with the neo$^r$ gene located between HS 1 and 2 of the human β-globin LCR. Bg/II-digested genomic DNA from randomly chosen G418-resistant D(HR9) hybrid clones was analyzed by Southern blotting using the junction and neo$^r$ probes. A correct targeting event in this hybrid yields a 10 kb fragment with both probes. A non-homologous insertion yields a 4.4 kb fragment with the junction probe, but not with the neo$^r$ probe. This fragment differs from the wild type 7.7 kb BglII fragment in DMh11)1, since there is a BglII site in the homologously inserted hygro$^r$ gene. The targeting frequency of the D(HR9)6-8 hybrid was similar to that of the DMh11)1 hybrid (11.5%). No clones with targeted insertions in the D(HR9)6-26 subclone were isolated.

EXAMPLE 7

Targeted integration into the human Hras locus in DT40/human microcell hybrids

To determine the frequency of targeted integration at other human loci in the DT40/human microcell hybrids, we transfected the D(Fneo)5 hybrid with a Hras targeting vector, pHrasPGKhygro, which is designed to insert a hygro$^r$ gene into the human Hras gene. This vector was constructed by cloning the 2.1 kb BglII fragment containing the hygromycin phosphotransferase gene driven by the phosphoglycerate kinase (PKG) promoter into the unique ClaI site of pHras6.6Bam (which contains a 6.6 kb BamHI genomic fragment encompassing the Hras gene) approximately 2.2 kb 3' of the Hras gene. Twenty-five micrograms of HindIII-linearized pHrasPGKhygro was added to 1.25×10$^7$ cells per ml of serum-free Dulbecco's Modified Eagle's Medium. The cells were electroporated at 25 µF and 550 volts, using a Bio-Rad Gene Pulser™ apparatus. The cells were incubated as a pool in nonselective medium for 24 hours, then plated into 4×96-well microtiter plates in DT40-conditioned medium containing 2.5 mg/ml G418. After 2 weeks, clones were picked individually and expanded. A typical transfection yielded 10–15 clones per 96-well microtiter plate, indicating that each clone picked represents an independent transfection event.

ScaI-digested genomic DNA from randomly chosen hygromycin B-resistant clones was analyzed by Southern blotting using Hras and hygro$^r$ probes. A correct targeting event in this hybrid reveals a new 15 kb ScaI fragment with both Hras and hygro probes, but not the endogenous 23 kb ScaI fragment. A non-homologous insertion results in the detection of both the endogenous 23 kb ScaI fragment and another variable-sized fragment representing the non-homologous insertion with the Hras probe, and the hygro probe detects only the variable-sized fragment. This is because the Hras probe is derived from the region of homology. The targeting frequency of D(Fneo)5 using this vector is 20%.

EXAMPLE 8

Construction of mouse microcell hybrids containing human chromosome 11 donated from a chicken/human microcell hybrid The M(Dh11) series hybrids were produced using DMh11)1 chicken/human microcell hybrid cells (APRT$^+$, Hm$^r$) as the donor. DMh11)1 cells were micronucleated in 0.015 µg/ml colcemid for 48 hours and enucleated by centrifugation through Percoil as described above. Microcells were fused to 2–3×10$^7$ recipient MEL (APRT$^-$, Hm$^s$) as above. The fusions were incubated as a pool in nonselective media for 24 hours, then plated at clonal density into 8×96-well microtiter plates in 0.2 ml/well of medium containing 500 µg/ml hygromycin B plus 40 µg/ml DAP. After 3–4 weeks, hybrid clones were picked individually and maintained in the same medium containing 0.25 µg/ml hygromycin B. The genotypes of M(Dh11) series hybrids were determined by FISH. A probe derived from total human DNA (from primary human diploid fibroblasts) hybridized to metaphase spreads revealed that 2 of 4 hybrids retained a single, apparently intact, human chromosome 11. The other 2 hybrids contained a small human chromosomal translocation into a mouse chromosome. DT40 genomic DNA was used as a FISH probe to determine whether, in addition to the human chromosomal material, any chicken DNA was transferred. Three of four hybrids had no detectable chicken DNA; however, one of the hybrids contained a small chicken chromosomal translocation into a mouse chromosome in <1% of the metaphase spreads. These results demonstrate the ability to transfer an intact human chromosome 11 from DT40 cells into MEL cells, thus permitting functional tests of targeted insertions in the human chromosome to be performed.

METHODS

Karyotype analysis

FISH karyotyping was performed on fixed metaphase spreads of the microcell hybrids essentially as described (Trask et al., *Am. J. Hum. Genet.* 48:1–15, 1991; and Brandriff et al., *Genomics* 10:75–82, 1991, which are incorporated by reference herein in their entirety). Human sequences were detected using labeled human diploid fibroblast genomic DNA as a probe. Chicken sequences were detected using labeled DT40 genomic DNA as a probe. Mouse sequences were detected using the RI/RII plasmid (Gebhard and Zachau, *J. Mol. Biol.* 157:453–471, 1982; which is incorporated by reference herein in its entirety), which contains a mouse repetitive element. Genomic DNA was biotinylated by nick translation (Gibco/BRL BioNick Kit) and hybridized in situ to denatured metaphase chromosome spreads for 12–24 hours. Probes were detected with avidin-fluorescein (Vector Labs, Burlingame, Calif.), and chromosomes were counterstained with propidium iodide (Sigma, St. Louis, Mo.). Signals were viewed through a Zeiss Axiophot fluorescence microscope, and photographs were taken with Kodak Ectachrome P 1600 color slide film.

Nucleic acid isolation and blot hybridization

High-molecular-weight genomic DNA was isolated as described (Miller et al., *Nucleic Acids Res.* 16:1215, 1988; which is incorporated by reference herein in its entirety), with the following modifications: 1×10$^7$ cells were pelleted and resuspended in 15 ml polypropylene tubes with 3 mls of nuclei lysis buffer (10 mM Tris-HCl/400 mM NaCl/2 mM Na$_2$EDTA, pH 8.2). The cell lysates were digested overnight at 37° C. with 0.1 ml of 25% SDS+0.5 ml of a Proteinase K solution (2 mg Proteinase K (Boehringer Mannheim, Indianapolis, Ind.) 1% SDS/2 mM Na$_2$EDTA, pH 7.5/5 µg/ml of RNase, DNase-Free (Boehringer Mannheim, Indianapolis, Ind.). Between 10 and 15 µg/ml of genomic DNA was digested by the indicated enzymes, size fractionated on 0.7% agarose gels, and transferred to Zetabind nylon membranes (Cuno, Meriden, Conn.) essentially as described by Southern (*J. Mol. Biol.* 98:503–517, 1975; which is incorporated by reference herein in its entirety). The DNA was immobilized on the filters using UV crossing, and the filters were washed at high stringency in a wash solution of 0.1×SSC/0.5% SDS at 65° C. for one hour. The filters were prehybidized at 42° C. in a prehybridization solution containing 50% formamide/5×SSPE/1%SDS/5×Denhardt's solution/10 µg/ml polyadenylic acid/polycytidilic acid (Pharmacia) for more than two hours. Purified plasmid inserts were labeled by random priming (Boehringer Mannheim, Indianapolis, Ind.), denatured, and hybridized with the filters in the same prehybridization solution overnight at 42° C. A 2.4 kb EcoRV fragment from the pOV12 plasmid (Lai et al., *Proc. Natl. Acad. Sci.* 77:244–248, 1980; which is incorporated by reference herein in its entirety) was used as a junction probe for the chicken ovalbumin gene analysis. The neo probe was derived from the 0.9 kb PstI fragment from pFR3neo plasmid which contained a neomycin phosphotransferase gene driven by the Friend virus long terminal repeat. A 0.8 kb BglII/NcoI fragment from the p5'ϵ2.6 plasmid served as the junction probe for the human β-globin LCR analysis (Kim et al., ibid.). A 0.9 kb ClaI-BamHI fragment from the pHras 6.6 Bam plasmid (containing a 6.6 kb BamHI genomic fragment encompassing the Hras gene) was used as a probe for the human ras analysis. The hygro probe was derived from the 1.2 kb NheI/AvaI fragment from the tgCMV/HyTk plasmid (Lupton et al. ibid.). After hybridization, the blots were washed sequentially under the following conditions: 2×SSC/0.1% SDS for 15 min at room temperature, 0.2× SSC/0.1% SDS for 15 min at room temperature, and 0.1× SSC/0.1% SDS for 30 minutes at 65° C. Autoradiography was carried out for 3 to 7 days at −70° C. using two intensifying screens and Kodak XAR film. Autoradiographs were scanned for reproduction using a Sharp Scanner JX-325 and Adobe Photoshop™ version 2.5 (Adobe Systems, Inc.).

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. An immortalized avian pre B cell line containing a mammalian chromosome, wherein said mammalian chromosome is stably maintained by a selectable marker.

* * * * *

UNITED STATES PATENT AND TRADEMARK OFFICE
CERTIFICATE OF CORRECTION

PATENT NO. : 5,543,319  Page 1 of 4
DATED : August 6, 1996
INVENTOR(S) : R.E.K. Fournier et al.

It is certified that error appears in the above-indentified patent and that said Letters Patent is hereby corrected as shown below:

| COLUMN | LINE | |
|---|---|---|
| Title page item, [56] col. 1 | Refs. Cited (Publs., Item #2) | "OSA" should read --USA-- |
| [56] col. 1 | Refs. Cited (Publs., Item #3) | "Kao, F-5." should read --Kao, F-T.-- |
| [56] col. 1 | Refs. Cited (Publs., Item #4) | After "Epner et al" insert --.-- |
| 1 | 60 | "arian" should read --avian-- |
| 2 | 22 | "recumbination." should read --recombination.-- |
| 4 | 18 | "ZIP-Neo SV(X)I" should read --ZIP-Neo SV(X)1-- |
| 4 | 53-54 | "between. 01 and 10 µ/ml." should read --between .01 and 10 µg/ml.-- |
| 4 | 66 | "percoil" should read --percoll-- |
| 6 | 1 | After "medium" insert --.-- |
| 7 | 50 | "108" should read --$10^8$-- |
| 8 | 1 | "28°or" should read --28° or-- |

UNITED STATES PATENT AND TRADEMARK OFFICE
CERTIFICATE OF CORRECTION

PATENT NO. : 5,543,319
DATED : August 6, 1996
INVENTOR(S) : R.E.K. Fournier et al.

It is certified that error appears in the above-indentified patent and that said Letters Patent is hereby corrected as shown below:

| COLUMN | LINE | |
|---|---|---|
| 8 | 8 | "*Cell* 11 38: 523-534, 1984 " should read --*Cell* 38:523-534, 1984-- |
| 8 | 8 | "hypo xanthine-guanine" should read --hypoxanthine-guanine-- |
| 8 | 31 | "(6Gibco/BRL)" should read --(Gibco/BRL)-- |
| 8 | 66 | "M(h 11)1" should read --M(h11)1-- |
| 10 | 2 | "ultracentfifuge" should read --ultracentrifuge-- |
| 10 | 10 | "Percoil." should read --Percoll.-- |
| 10 | 33 | "10% tryprone" should read --10% tryptone-- |
| 10 | 42 | "D(Mh1 1)1," should read --D(Mh11)1,-- |
| 10 | 49 | "11 q21-22" should read --11q21-22-- |
| 11 | 19 | "D(Mh1 1 )1," should read --D(Mh11)1,-- |
| 11 | 63 | "DMh11)1," should read --D(Mh11)1,-- |
| 12 | 5 | "s-globin" should read --ε-globin-- |
| 12 | 10 | "(DMh11)1," should read --(D(Mh11)1,-- |

UNITED STATES PATENT AND TRADEMARK OFFICE
CERTIFICATE OF CORRECTION

PATENT NO. : 5,543,319
DATED : August 6, 1996
INVENTOR(S) : R.E.K. Fournier et al.

It is certified that error appears in the above-indentified patent and that said Letters Patent is hereby corrected as shown below:

| COLUMN | LINE | |
|---|---|---|
| 12 | 14 | "p5'ε FneoF/tk" should read --p5'εFneoF/tk-- |
| 12 | 21 | "microtiler" should read --microtiter-- |
| 12 | 22 | "Bg lII" should begin a new paragraph. |
| 12 | 23 | "Dmh11)1" should read --D(Mh11)1-- |
| 12 | 30 | "Dmh11)1" should read --D(Mh11)1-- |
| 12 | 49 | "HS 1" should read --HS1-- |
| 12 | 50 | "Bg/II-digested" should read --*Bgl*II-digested-- |
| 12 | 57 | "DMh11)1," should read --D(Mh11)1,-- |
| 12 | 59 | "DMh11)1" should read --D(Mh11)1-- |
| 13 | 9 | "HindlII-" should read --*Hind*III--- |
| 13 | 42 | "DMh11)1" should read --D(Mh11)1-- |
| 13 | 43 | "DMh11)1" should read --D(Mh11)1-- |
| 13 | 45 | "Percoil" should read --Percoll-- |
| 14 | 26 | "P 1600" should read --P1600-- |

UNITED STATES PATENT AND TRADEMARK OFFICE
CERTIFICATE OF CORRECTION

PATENT NO.    : 5,543,319
DATED         : August 6, 1996
INVENTOR(S)   : R.E.K. Fournier et al.

It is certified that error appears in the above-indentified patent and that said Letters Patent is hereby corrected as shown below:

| COLUMN | LINE | |
|---|---|---|
| 14 | 39 | After "µg" delete --/ml-- |
| 14 | 41 | After "µg" delete --/ml-- |
| 14 | 49-50 | "prehybfidized" should read --prehybridized-- |
| 14 | 67 | "6.6 Barn plasmid" should read --6.6 *Bam* plasmid-- |

Signed and Sealed this

Fourth Day of February, 1997

Attest:

BRUCE LEHMAN

Attesting Officer          Commissioner of Patents and Trademarks